(12) United States Patent
Molina et al.

(10) Patent No.: US 7,946,420 B2
(45) Date of Patent: May 24, 2011

(54) PACKAGE CONTAINING A WINDOW AND A PERFORMANCE CHARACTERISTIC INDICATOR

(75) Inventors: Lilkar Zugeil Molina, Deerfield Township, OH (US); John Thomas Milby, Harrison Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/714,952

(22) Filed: Mar. 1, 2010

(65) Prior Publication Data

US 2010/0147721 A1 Jun. 17, 2010

Related U.S. Application Data

(63) Continuation of application No. 11/650,822, filed on Jan. 8, 2007, now Pat. No. 7,694,818, which is a continuation of application No. 10/607,683, filed on Jun. 27, 2003, now Pat. No. 7,185,761, which is a continuation-in-part of application No. 10/011,192, filed on Dec. 7, 2001, now Pat. No. 6,601,705.

(51) Int. Cl.
*B65D 85/16* (2006.01)

(52) U.S. Cl. ............... 206/494; 206/440; 206/459.5

(58) Field of Classification Search ............ 206/438, 206/440, 494, 459.5, 812, 775–778, 781; 40/312; 383/66, 106, 207; 604/358, 385.02
See application file for complete search history.

(56) References Cited

U.S. PATENT DOCUMENTS

| | | |
|---|---|---|
| 1,844,189 A | 2/1932 | Stuart |
| 3,306,437 A | 2/1967 | Nelson |
| 3,351,209 A | 11/1967 | Kofoed et al. |
| 3,977,452 A | 8/1976 | Wright |
| 4,556,146 A | 12/1985 | Swanson et al. |
| RE32,443 E | 6/1987 | Kalal |
| 4,696,050 A | 9/1987 | Sengewald |
| 4,801,005 A | 1/1989 | Hahn |
| 4,934,535 A | 6/1990 | Muckenfuhs |
| 4,966,286 A | 10/1990 | Muckenfuhs |
| D312,208 S | 11/1990 | Sorkin |

(Continued)

FOREIGN PATENT DOCUMENTS

DE  39 07 291 A1  9/1990

(Continued)

OTHER PUBLICATIONS

BPAI Decision for U.S. Appl. No. 11/130,674 dated Mar. 23, 2009; P&G Case AA551C2; Hirotsu; filing date May 17, 2005.

(Continued)

*Primary Examiner* — Luan K Bui
(74) *Attorney, Agent, or Firm* — Amanda T. Barry

(57) ABSTRACT

A package including a container having a layer with an interior surface and an exterior surface. The layer forms an interior space. The container includes a window on only a portion of the exterior surface. The container contains within the interior space one or more absorbent articles each having substantially the same absorbent capacity. Each absorbent article is individually wrapped in a wrapper. The exterior surface of the container has a signal color corresponding to the absorbent capacity, and each of the wrappers has a substantially similar signal color in the form of a design. In addition, only a portion of the wrapper can be viewed through the window.

20 Claims, 6 Drawing Sheets

U.S. PATENT DOCUMENTS

| | | | |
|---|---|---|---|
| 4,991,980 A | 2/1991 | Cohen | |
| 5,044,492 A | 9/1991 | Auerbach | |
| 5,050,742 A | 9/1991 | Muckenfuhs | |
| 5,290,269 A | 3/1994 | Heiman | |
| 5,326,575 A | 7/1994 | Spaulding | |
| 5,344,027 A | 9/1994 | Kaplan | |
| 5,360,512 A | 11/1994 | Blum | |
| 5,361,905 A | 11/1994 | McQueeny | |
| 5,413,568 A | 5/1995 | Roach et al. | |
| 5,435,459 A | 7/1995 | Huck et al. | |
| 5,458,590 A | 10/1995 | Schleinz et al. | |
| 5,464,285 A | 11/1995 | Anderson | |
| D371,707 S | 7/1996 | Miles | |
| D372,272 S | 7/1996 | Frisch | |
| 5,569,228 A | 10/1996 | Byrd | |
| 5,630,512 A | 5/1997 | Wells | |
| 5,681,301 A | 10/1997 | Yang et al. | |
| 5,743,407 A | 4/1998 | Williams | |
| 5,839,585 A | 11/1998 | Miller | |
| 5,865,322 A | 2/1999 | Miller | |
| 5,897,542 A | 4/1999 | Lash | |
| 5,924,559 A | 7/1999 | Carrel | |
| 5,931,304 A | 8/1999 | Hammond | |
| 5,947,297 A | 9/1999 | Aoki | |
| 5,947,302 A | 9/1999 | Miller | |
| 5,947,943 A | 9/1999 | Lee | |
| 5,967,665 A | 10/1999 | MacDonald | |
| 6,022,677 A | 2/2000 | Bourdelais et al. | |
| 6,024,219 A | 2/2000 | Froehlich et al. | |
| 6,074,376 A | 6/2000 | Mills | |
| 6,077,579 A | 6/2000 | De Laforcade | |
| 6,093,027 A | 7/2000 | Unger et al. | |
| 6,152,305 A | 11/2000 | Green | |
| 6,168,028 B1 | 1/2001 | Telesca | |
| 6,293,932 B1 | 9/2001 | Balzar et al. | |
| 6,318,555 B1* | 11/2001 | Kuske et al. | 206/494 |
| 6,328,158 B1 | 12/2001 | Bisbal et al. | |
| 6,368,113 B1 | 4/2002 | Unger et al. | |
| 6,454,095 B1* | 9/2002 | Brisebois et al. | 206/494 |
| 6,488,202 B1 | 12/2002 | Seitz et al. | |
| 6,568,530 B2 | 5/2003 | Takahashi et al. | |
| 6,601,705 B2 | 8/2003 | Molina et al. | |
| 6,612,846 B1 | 9/2003 | Underhill et al. | |
| 2002/0046079 A1 | 4/2002 | Stavrulov | |
| 2002/0049418 A1 | 4/2002 | Brown | |
| 2002/0072723 A1 | 6/2002 | Ronn et al. | |
| 2002/0156448 A1 | 10/2002 | Steger et al. | |
| 2004/0102748 A1* | 5/2004 | Hirotsu | 206/438 |
| 2005/0209576 A1 | 9/2005 | Hirotsu | |
| 2007/0108078 A1 | 5/2007 | Molina et al. | |
| 2008/0011642 A1 | 1/2008 | Oi et al. | |

FOREIGN PATENT DOCUMENTS

| | | |
|---|---|---|
| EP | 0 986 996 A2 | 3/2000 |
| EP | 1 174 104 A1 | 1/2002 |
| EP | 1 153 838 B1 | 10/2004 |
| WO | WO 93/16929 A1 | 9/1993 |
| WO | WO 96/22756 A2 | 8/1996 |
| WO | WO 97/49618 A2 | 12/1997 |
| WO | WO 02/30347 | 4/2002 |

OTHER PUBLICATIONS

Brazilian Product Launch Round Up-Johnson & Johnson, OTC LatinA, n. 12, p. 389, Jun. 1996.
Lil-lets Updates Applicator Range, Packaging Revamp for Lil-lets Range, Chmist & Druggist (CTD) p. 584, Oct. 26, 1996.
Tampax Tampons—Multi-pack of Super, Regular Lites, Product Alert, v27, N16, Aug. 25, 1996.
HTTP://MUM.ORG/FREEDBOX.HTM—Box of Tampons at the Museum of Menstruation and Women's Health—2 pages.
Product Images on CD.
PCT International Search Report dated Mar. 19, 2003.

* cited by examiner

PACKAGE CONTAINING A WINDOW AND A PERFORMANCE CHARACTERISTIC INDICATOR

CROSS REFERENCE TO RELATED APPLICATIONS

This application is a continuation of U.S. application Ser. No. 11/650,822, filed Jan. 8, 2007, U.S. patent Ser. No. 7,694,818, which is a continuation of U.S. Pat. No. 7,185,761 application Ser. No. 10/607,683 filed on Jun. 27, 2003, U.S. Pat. No. 7,185,761, which is a continuation-in-part of application Ser. No. 10/011,192 filed on Dec. 7, 2001, U.S. Pat. No. 6,601,705.

FIELD OF INVENTION

The present invention relates to a package for containing and dispensing absorbent articles. Proper selection and use of such articles is communicated by means of using a distinctive coding system associated with the articles and their packaging, and a window that displays the thickness of the article. In preferred embodiments, the invention relates to absorbent articles for absorbing bodily fluids, especially menses.

BACKGROUND OF THE INVENTION

Surprisingly, some of the problems associated with the proper selection and use of such articles is traceable to modern developments in the technologies used to improve consumer satisfaction. Improvements made in modern absorbent articles in an effort to increase in-use comfort and consumer satisfaction have resulted in the proliferation of sizes, shapes, conformations and brands in the field of disposable absorbent articles such as feminine care articles. Because of the proliferation of sizes, shapes, conformations and brands in the field of disposable absorbent articles, customers have difficulty differentiating between the many types of articles and the variations of article characterizations within these article types.

Differentiation and selection of consumer articles on store shelves is difficult due to the many types of articles and variations of article characterizations within these article types. Differentiation and selection of articles is also particularly difficult when the artwork, color, and/or shape of the package changes. In addition, differentiation and selection of catamenial articles on store shelves are particularly difficult due to the many choices of article absorbencies such as: light absorbency, regular absorbency, and extra absorbency and article configurations, for example, daytime articles, nighttime articles, winged versions and the like.

Consumers do not make the proper selection because they are uncertain of the size, shape, and bulk of the absorbent article. A contributing factor to the consumer's uncertainty occurs when a consumer is not able to estimate by visual inspection the size, shape, and bulk of absorbent articles such as baby diapers, sanitary napkins, and adult incontinence garments. As a result of the consumer's uncertainty, the consumer may make an inadvertent selection of a low absorbency catamenial for use on a high flow day, which can result in considerable dissatisfaction. Whatever the reason, it is problematic for a manufacturer when a well-designed article is judged by its users to be sub-optimal in performance, when the real problem stems from selection errors, which result in misuse.

Moreover, the consumer may solve the problem of lack of visual inspection by undesired means. Where the package does not show the article visually, consumers may resort to opening the package to visually inspect the article. Although the consumer may be satisfied about visually inspecting the article, the package of articles are left open and may not be resalable. Thus, allowing the customer to visually inspect the article through the package is a benefit to the merchant and/or owner.

Proper selection of consumer articles requires explicit labeling and/or instructions. Despite considerable attention being given to such matters, mistakes continue to be made by consumers. In some instances, the consumer may be inattentive, unable to determine the thinness or thickness of the article, or may have a limited amount of time to make a selection of a given article. In others, linguistic difficulties may contribute to improper selection and usage.

Typical instructional matter pertaining to the proper selection and use of absorbent articles conventionally comprises printed text, pictures, diagrams, labels, and combinations thereof. The objective of any optimal instructional matter is to be univocal, i.e., to convey a message regarding proper selection and usage in such a clear, concise, and exact manner that essentially any user, regardless of distractions or adverse conditions, is prompted to choose and employ the article correctly.

Often color is used to convey a particular performance characteristic of a given article. For example, at least one manufacturer of catamenial tampons uses color-based signals on both the outer packaging and the wrapper of such tampons to denote absorbent capacity. In such articles, different colors are used to represent different article characteristic levels (in this case absorbency). For example, a green band on the package and wrapper of a tampon might signal a "super" absorbency tampon, while a blue band might signal a "regular" absorbency tampon.

Moreover, a woman's menstrual cycle is typically characterized by initial "mild flow" days, followed by "medium flow" days, and concluding with "low flow" days. In order to meet the need for feminine protection during the entire sequence, at least one manufacturer has begun the sale of kits, which contain multiple disposable absorbent catamenials having extra, regular, and light absorbent capacities, respectively. In this way, the need for protection can be met with as little discomfort as possible to the user over the entire menstrual cycle. Alternatively, light, regular, and extra absorbency articles can be sold separately or as a complete line of articles. Compliance with the prescribed sequence of usage is a prerequisite for the successful completion of any multi-phase regimen. This also applies to the aforesaid kits.

Accordingly, the proper usage of extra, regular, or light capacity absorbent articles begins with the proper selection of such articles. The present invention provides an easy and intuitive package for selecting the proper absorbency, which provides a consumer benefit and ensures that the right article will be taken home.

SUMMARY OF THE INVENTION

A package including a container having a layer with an interior surface and an exterior surface is provided. The layer forms an interior space. The container includes a window on only a portion of the exterior surface. The container contains within the interior space one or more absorbent articles each having substantially the same absorbent capacity. Each absorbent article is individually wrapped in a wrapper. The exterior surface of the container has a signal color corresponding to the absorbent capacity, and each of the wrappers has a substantially similar signal color in the form of a design. In addition, only a portion of the wrapper can be viewed through the window.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in conjunction with the accompanying drawings, in which:

DETAILED DESCRIPTION OF THE INVENTION

Figure 1:
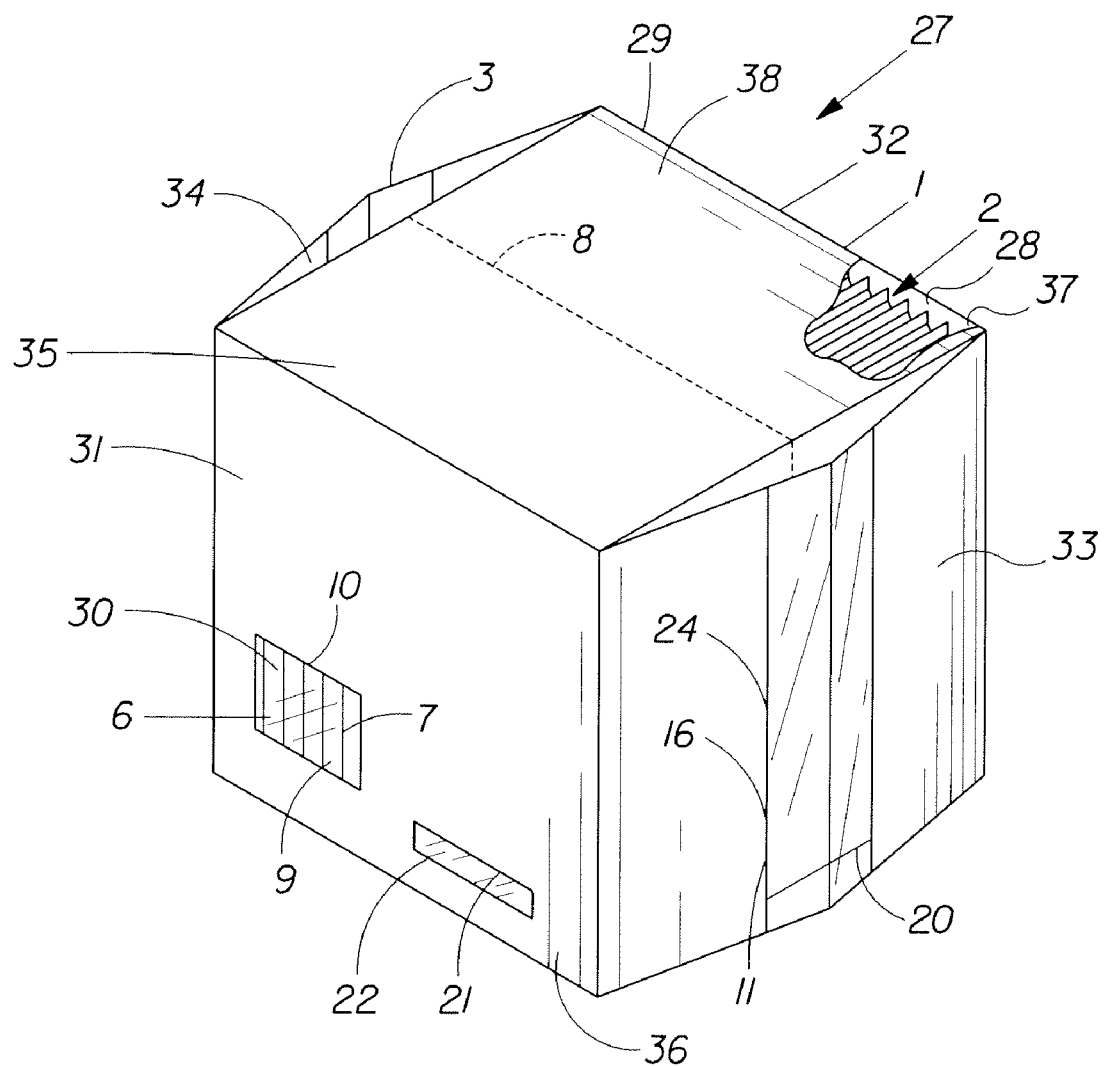
FIG. 1 is the front view of a container of thin maxi sanitary napkins.

Referring primarily to FIG. 1, the package illustrated is a flexible container 27 made from a layer 29. Layer 29 has an interior surface and an exterior surface. Layer 29 is folded and secured together. The container 27 has a length, width, and a height dimension. The container has a front face 31, a rear face 32, a side face 33, a side face 34, a top face 35, and a bottom face 36. The container may be any shape known in the art. For example, the container may have a polyhedral shape defining or forming a polyhedral enclosure.

The interior 28 of the container 27 defines an interior space 2 for containing absorbent articles 6. The absorbent articles 6 may all be identical to one another or may be different absorbent articles 6.

The absorbent articles 6 are arranged to form a stack 30 within the interior space 2 of the container 27. The articles 6 may be stacked in any direction. As used herein, the term "stack" is meant an orderly pile. For example, the articles may be stacked vertically, horizontally, or at any angle inside the interior 2 of the container 27.

The container 27 may include at least one gusset 3 integrally formed with at least one side face 33 or side face 34, and a means for accessing the interior space 2 for easy access to the article 6. The mechanism or means for accessing the interior space 2 can be a line of perforations 8. In other alternative embodiments, a means for accessing the interior space 2 can be tabs and adhesive openings. The mechanism or means for accessing the interior space 2 can be any means known in the art.

The layer 29 may be composed of different materials or may be composed of substantially the same type of material. The layer 29 may be composed of one layer 29 or a laminate. The material can comprise of blown or cast film in a blend of low density polyethilene and linear low density poliethylene, metallocenes, ethylene vinyl acetate, surlyn, polyethylene terephtalate, biaxially oriented polypropylene, and/or nylon.

In its broadest aspect, the present invention relates to color and/or design indicators for use with absorbent articles and the absorbent articles' corresponding packaging. The use of different colors can be used to signal absorbency or other article performance characteristics such as size and strength.

An article's performance characteristic is the consumer recognition of the execution of a particular characteristic of the article. As used herein, the term "characteristic" refers to any distinguishing trait, quality, or properties of the article. Within the context of this description, the article's performance characteristic can be indicated by the color, shape, size, or the like of the article. For example, an outer package contains super absorbent sanitary pads individually wrapped in an orange wrapper. The orange color of the wrapper is the indicator for the performance characteristic, which indicates super absorbency. The orange color of the wrapper provides the consumer with an easy identification of the article. The window in the outer package reveals any portion of the orange wrapper and/or the thickness of the sanitary napkin. The thickness of the product is also an indicator of the product's performance.

The term "color," as used herein, is a visual effect resulting from the eye's ability to distinguish the different wavelengths or frequencies of light. The apparent color of an object depends on the wavelength of the light that it reflects. In white, or normal light, an opaque object that reflects all wavelengths appears white and one that absorbs all wavelengths appears black. To describe a color with reasonable accuracy, three basic properties have been designated to identify the dimensions, or qualities, of color: 1) hue, the name of a color as found in its pure state in the spectrum i.e., that attribute of colors that permits them to be classified as red, yellow, green, blue, etc., or as an intermediate between any contiguous pair of colors; 2) value, the lightness or darkness of a color; 3) and intensity, the degree of purity or strength of a color. While a wide palette of colors can be employed herein, it is preferred to use a member selected from the group consisting of white, orange, purple, lavender, red, green, blue, yellow, violet, gray, brown, and black.

Referring to FIG. 1, at least one signal color 7 is placed on the wrapper 9 of the article 6 and at least one signal color 21 is placed on the exterior surface 38 of the outer container 1. Signal colors 7, 21 may be placed in any graphic or shape such as droplets, circles, parallelepipeds, or the like. The signal colors 7, 21 may be in any convenient size. The signal color 7 may encompass the entire wrapper 9 or may encompass part of the wrapper 9. Likewise, the signal color 21 may encompass the entire container 27 or may encompass part of the container 27.

Figure 2A:
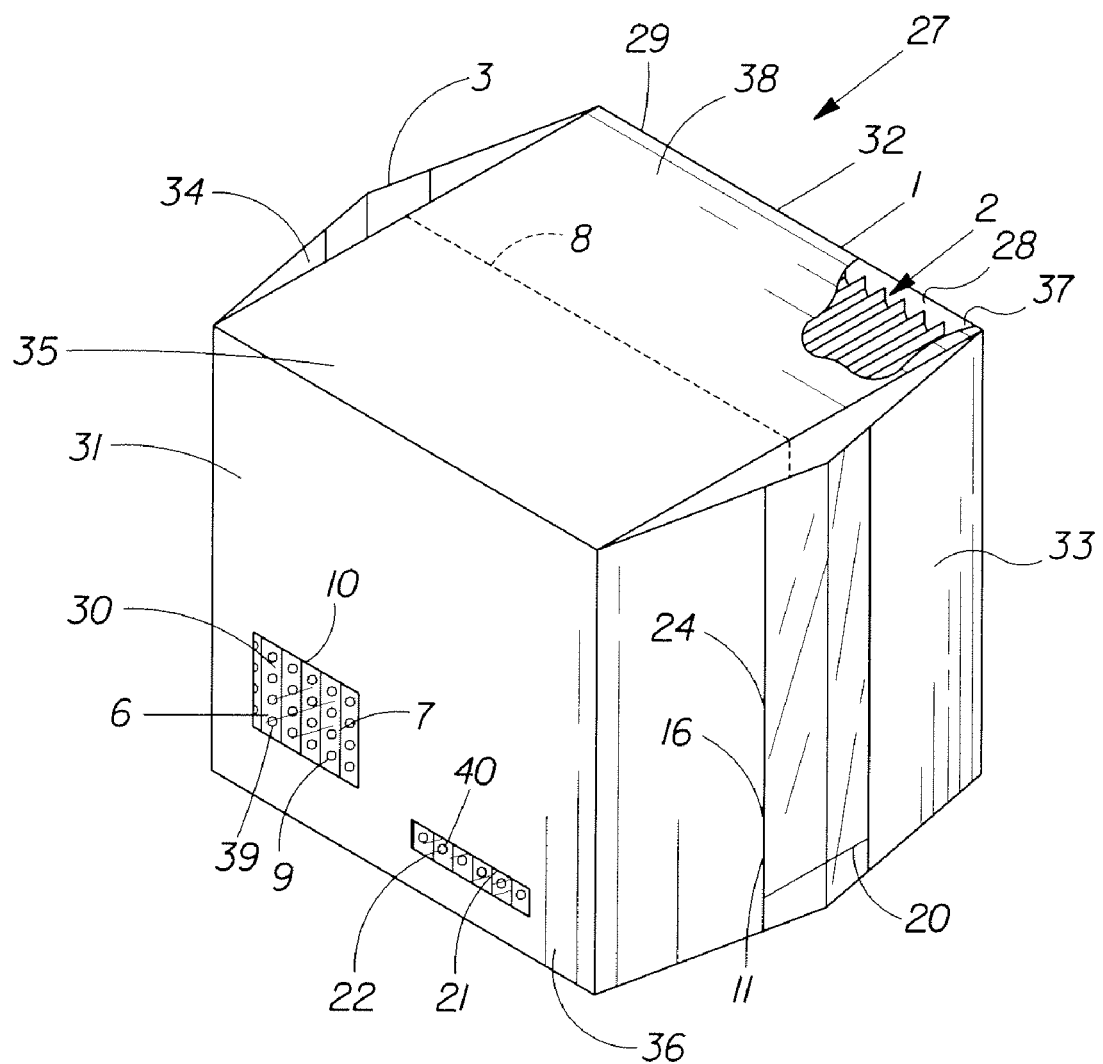
FIG. 2a is a perspective view of an alternative embodiment of a container.
Figure 2B:
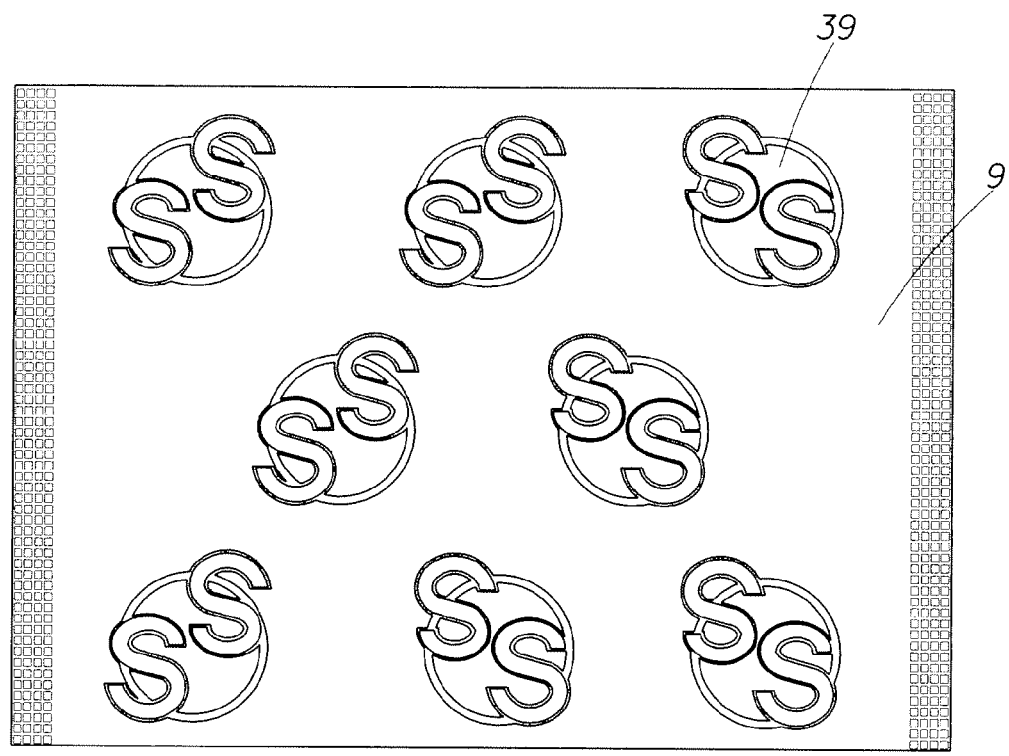
FIG. 2b is a perspective view of a wrapper.
Figure 2C:
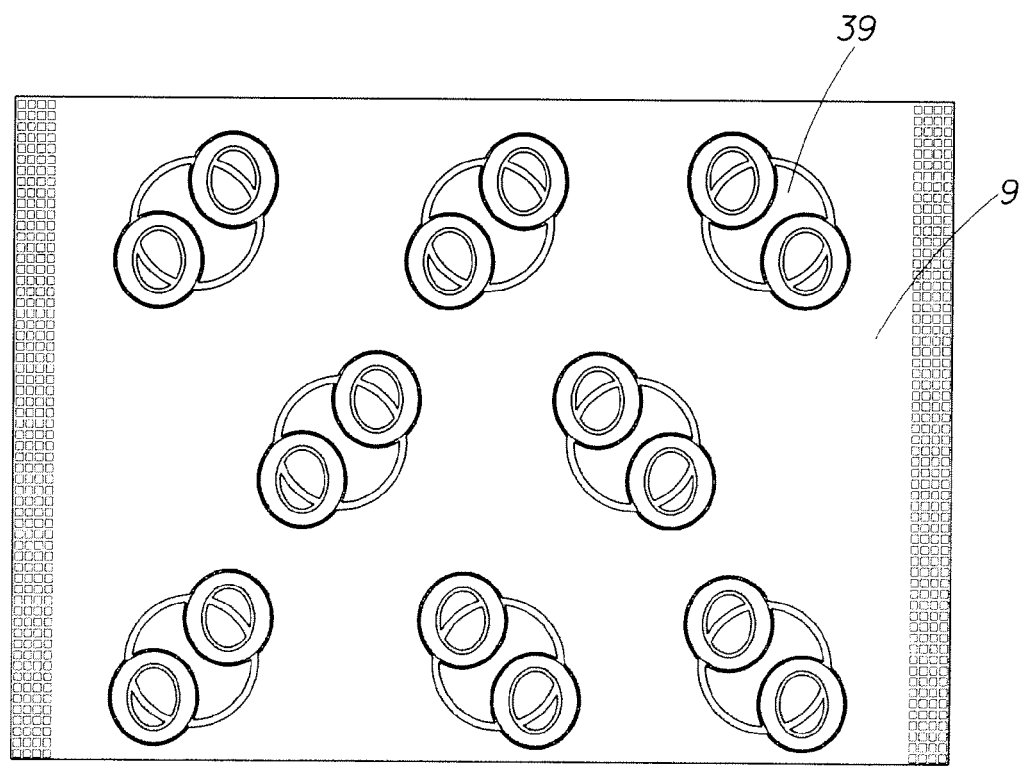
FIG. 2c is a perspective view of a wrapper.

Referring to FIG. 2a, the signal colors 7 on the wrapper 9 may encompass a design 39 and the signal color 21 on the exterior of the container 27 may encompass a design 40. The designs 39, 40 can be any shape such as rectangular, square, elliptical, polygonal, triangular, etc. The design 39, 40 can encompass one shape or a combination of the afore-mentioned shapes. The design 39, 40 can encompass one color or several colors. As seen in FIG. 2b and FIG. 2c, the wrapper 9 encompasses a design 39.

Referring to FIG. 2a, the signal color 7 and/or design 39 and the signal color 21 and/or design 40 on the graphic 22 of the exterior of the container 27 may be variations of intensity and contrasting colors. When there is a design 39 on the wrapper 9 and/or article 6 to indicate a product characteristic and the design 39 has at least one color and/or shape, the signal color 7 on the wrapper 9 can be substantially similar to the signal color 21 on the exterior of the container 27. Moreover, when there is a design 39 on the wrapper 9 to indicate a product characteristic and the design 39 has at least one shape, the shapes included in the design 40 on the graphic 22 of the exterior of the container 27 can be substantially similar to any of the shapes included in the design 39 on the wrapper 9. If the design 39 has colors, at least one color of the signal colors 7 is color coordinated with at least a portion of the exterior of the container 27. In an alternative embodiment, the color and/or shape on the wrapper 9 can have a different intensity than the color and/or shape on the exterior of the container 27. By intensity, is meant the purity of the hue. For example, an intense red is one that is a very strong, pure red color. When a lighter or darker color is added to a color, the intensity will be less bright. In an alternative embodiment, the color and/or shape on the wrapper 9 can have a contrasting color than the color and/or shape on the exterior of the container 27. By contrast, is meant one light element and two dark elements.

Likewise, when there is a design 40 on the graphic 22 of the exterior container 27 to indicate a product characteristic and the design 40 has at least one color and/or shape, the signal color 21 on the exterior container 27 can be substantially similar by way of color and/or shape to the signal color 7 on the wrapper 9. Similarly, when there is a design 40 on the exterior of the container 27 to indicate a product characteristic and the design 40 has at least one shape, the shapes included in the design 39 on the wrapper 9 can be substantially similar to any of the shapes included in the design 39 on the wrapper 9. If the design 40 has colors, at least one color of the signal colors 21 is color coordinated with at least a portion of wrapper 9.

Figure 2D:
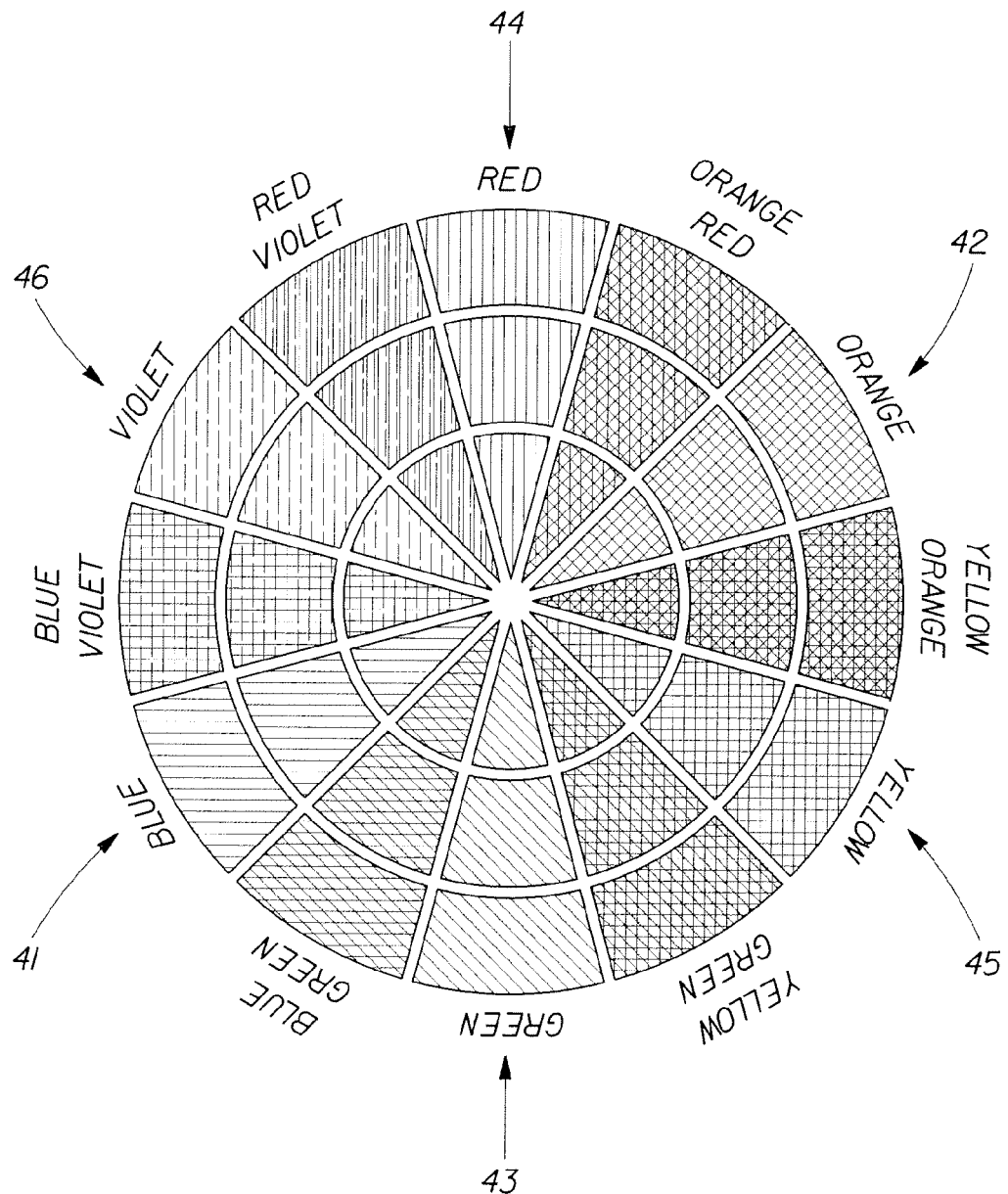
FIG. 2d is a perspective view of the color spectrum.

By color coordinated, is meant the color of the design 39 on at least a portion of the wrapper 9 and the color of the design 40 on at least a portion of the exterior of the container 27 may be complimentary, analogous, warm/cool colors, monochromatic, and/or neutral. Referring to FIG. 2d, by complimentary colors, is meant those colors which are directly opposite one other in the color spectrum or wheel. For example, blue 41 is the opposite of orange 42. Because blue 41 is the opposite of orange 42, gold, rust, and brown compliment shades of blue 41. By analogous colors, is meant those colors which are next to each other on the color wheel. For example, blue 41 could be color coordinated with green 43. Referring to FIG. 2d, by warm and cool colors, is meant families of analogous colors. Warm colors are colors such as red 44, orange 42, and yellow 45. Cool colors are colors such as green 43, blue 41, and violet 46. Warm and cool colors may be mixed together. For example two warm colors on the wrapper 9 may be selected to match with one cool color on the exterior of the container 27. In another example, two cool colors on the wrapper 9 may be color coordinated with a warm color on the exterior of the container 27. By monochromatic, is meant all one color, but different shades, tones, or tints. By neutral, is meant shades of white, black, gray, or beige.

Referring to FIG. 1, the signal color 7 on the wrapper 9 of the article 6 and the signal color 21 on the exterior of container 27 are substantially similar or the same color. The colors are substantially similar if the colors closely resemble each other or if one color has the possibility of being mistaken for the other. A color is the "same" if the color corresponds so closely that is it indistinguishable.

When so employed, the signal colors 7, 21 provide an easy and intuitive method for selecting the proper absorbent article 6 (for example, that with the desired absorbency). When the signal color 7 is used on the wrapper 9 of the article 6, the signal color 7 provides a method for selecting the proper absorbent articles 6. In addition, the signal color 7 aides the consumer in identifying the absorbent article 6 when the absorbent article 6 is removed from the container 27 and placed in the bathroom drawer, purse, etc. An important advantage of having the same or substantially the same color for both the signal color 7 and the signal color 21 placed on the exterior surface 38 of container 27 is that the user is provided with the desired intuitive, selection, and usage means which is the object of this invention.

Many embodiments of absorbent articles are well-known in the art. Sanitary napkins, sanitary panties, interlabial devices, intravaginal devices (tampons), adult incontinence articles, infant diapers, pantiliners, and the like, have been described in the extensive patent literature and many such articles are in the stream of commerce. See, for example: for sanitary napkins U.S. Pat. No. 4,463,045 issued to Ahr et al. and U.S. Pat. No. 4,556,146 issued to Swanson et al.; for tampons such as U.S. Pat. No. 5,087,239 issued to Beastall et al. and U.S. Pat. No. 5,279,541 issued to Frayman et al.; and for diapers such as U.S. Pat. No. 4,573,986 issued to Minetola et al.; U.S. Pat. No. 4,695,278 issued to Lawson; U.S. Pat. No. 4,081,301 issued to Buell; and U.S. Pat. No. 4,515,595 issued to Kievit. Such articles contain an absorbent structure, typically in the form of a "core" or pad. Various fluid-permeable top layers, fluid-impermeable back layers, panty-protective "wings," tape fasteners and the like, are optionally used to construct elements for such articles and are all within the experience of those of ordinary skilled in the art.

Likewise, the manufacture of such articles having differing absorbent capacities (here, for the sake of simplicity, designated as "extra," "regular," and "light") is also a matter of routine. By way of example and not intending to limit the present invention, a modern "extra" absorbent article will typically have an absorbent core comprising an absorbent gelling materials ("AGM") in combination with a cellulosic batt of fibers. Conversely, a "light" absorbent article may comprise only the fibrous batt, without the AGM. A "medium" absorbent article may contain some intermediate level of AGM.

Again, without intending to limit the present invention, the following capacities (for menses) of absorbency designated as "extra," "regular," and "light," respectively, will typically, but non-quantitatively, fall within ranges.

For Ultra Thin Pads

| Size | Retained Capacity |
| --- | --- |
| Regular Length | 25-30 grams |
| Long Length | 30 grams |
| Long Overnights | 34-35 grams |

For Interlabial Devices:

| | Article | Article | Retained Capacity | |
| --- | --- | --- | --- | --- |
| Size | Length (mm) | Caliper (mm) | g @ .25 psi | g @ 1.0 psi |
| Light | 76 (−16%) | 4.5 | 3.7 (−35%) | 2.7 (−32%) |
| Regular | 91 (Base) | 5.5 | 5.7 (Base) | 4.0 (Base) |
| Long | 106 (+16%) | 6.5 | 10.5 (+84%) | 6.7 (+67%) |

For Tampons:

| Size | Retained Capacity |
| --- | --- |
| Junior absorbency: | <6 grams |
| Regular absorbency: | 6-9 grams |
| Super absorbency: | 9-12 grams |
| Superplus absorbency: | 12-15 grams |

-continued

| Size | Retained Capacity |
| --- | --- |

For Disposable Diapers (as Urine):
There are no mandatory absorbency ranges for diapers. The diapers are marketed according to weight:
Premie
Newborn
Small
Small-Medium
Large
Extra-Large.

Of course, the absorbent values of such capacities can be adjusted by the manufacturer, as evidenced by the fact that it has become commonplace to designate absorbency using various descriptive, but non-quantitative, terms such as "mini," "regular," "super," "maxi," "overnight," and the like, as a guide to selection based on the user's conception of expected absorbency performance, and perceived need.

The following examples illustrate the practice of the invention, but are not intended to be limiting thereof.

EXAMPLE I

Figure 3:
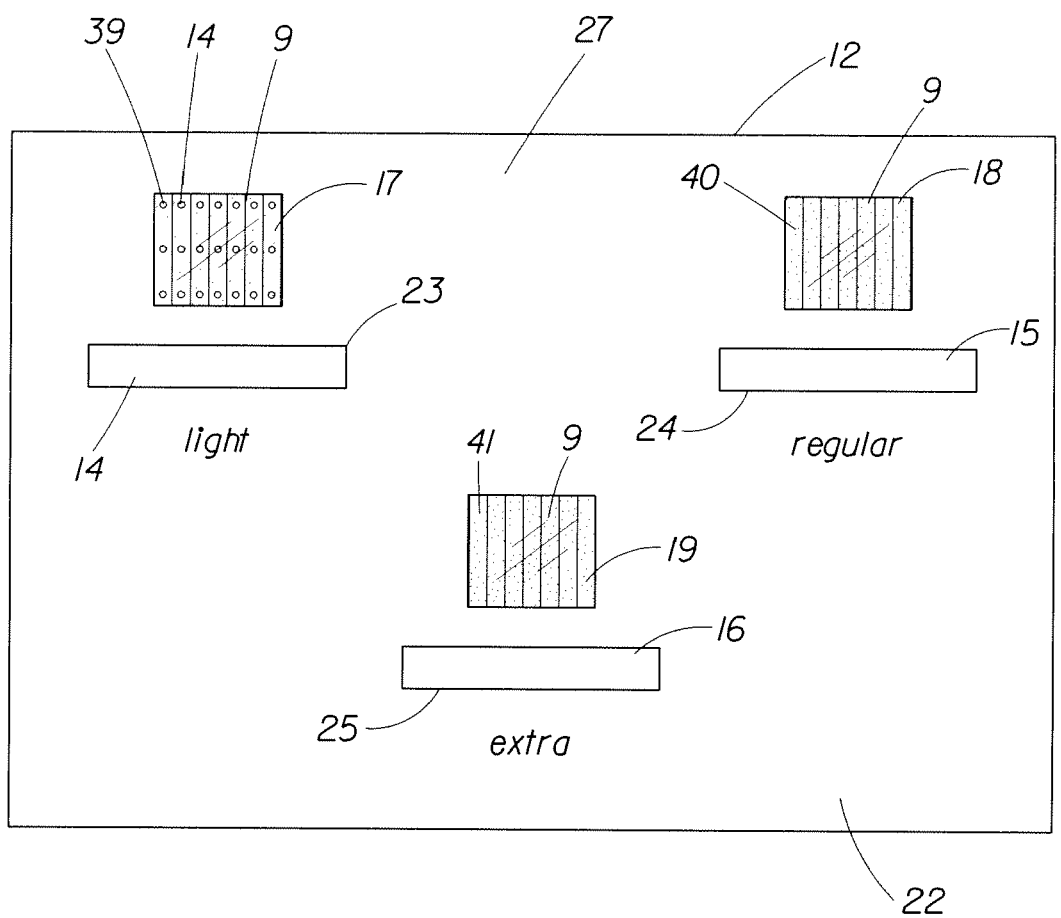
FIG. 3 is a front view of a container for a kit containing maxi sanitary napkins, thin maxi sanitary napkins, and ultra sanitary napkins.

Although the number of types of absorbent articles may vary as desired, three types of sanitary napkins are shown in FIG. 3. As shown in FIG. 3, a "multi-pack" kit 12 comprising light, regular, and extra absorbency sanitary napkins is prepared. The kit 12 consists of three different signal colors 14, 15, and 16 to denote the respective absorbencies of the light, regular, and extra absorbency sanitary napkins within the kits. The signal color white 14 denotes light absorbency. The white signal color 14 is displayed on the graphic 23 which is on the exterior container 27. The signal color 14 and a distinctive design 39 is displayed on the wrapper 9. The signal color gray 15 denotes regular absorbency. The gray signal color 15 is displayed on the graphic 24 which is on the exterior container 27. The signal color 15 and a distinctive design 40 is displayed on the wrapper 9. The signal color black 16 denotes extra absorbency. The black signal color 16 is displayed on the graphic 25 which is on the exterior container 27. The signal color 16 and a distinctive design 41 is displayed on the wrapper 9 of the article. The container of the "multi-pack" kit has three windows 17, 18, and 19, which reveals the thickness of each type of sanitary napkin by allowing a consumer to see the absorbent articles through the windows.

Figure 4:
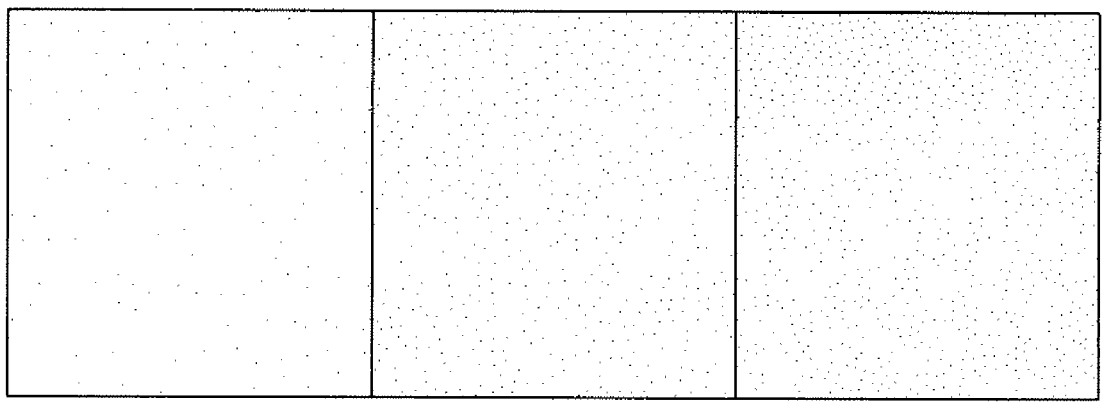
FIG. 4 is the color line for white, gray, and black.

In an alternate mode, the kit 12 can comprise a combination of pantiliners, sanitary napkins, and interlabial devices, each appropriately color-coded to indicate their respective differences in absorbencies in the manner described above. FIG. 4 is the color legend for white, black, and gray.

EXAMPLE II

Another example is a diaper that has the performance characteristic of size. Multiple diapers are separately packaged in film unit wrappers having the colors: green, pink, purple, blue, and yellow. The Premie-sized diapers are packaged in green wrappers. The Newborn-sized diapers are packaged in pink wrappers. The Small-sized diapers are packaged in purple wrappers. The Small-Medium-sized diapers are packed in blue wrappers. The Large-sized diapers are packed in yellow wrappers.

As shown in FIG. 1, window 10 is used to indicate and reinforce performance characteristics by matching the color of the performance characteristic on the exterior of container 27 with the performance characteristic of the wrapper 9 of the article 6 or with just the article 6. The window 10 allows the consumer to know in advance the quality and characteristic of the product inside of the container 27. The window 10 empowers the consumer to quickly pick the right article 6, which in turn matches the value expectations of the article 6.

Referring primarily to FIG. 1, one or more windows 10 may be placed on its packaging in any shape such as droplets, circles, parallelepipeds, or the like. The window 10 may encompass the entire article or may encompass part of the article 6. Specifically, window 10 may be placed anywhere on the container 27, e.g. on the top, sides, or bottom, or all three. Furthermore, the overall trade dress of the article may use the window 10 in a variety of ways. When so employed, the window 10 provides an easy and intuitive method for identifying and selecting the proper article 6 (for example, that with the desired absorbency). Another benefit of the window is aiding the consumer in color recognition to choose the right article 6 and identify the proper thickness of the article 6. Additionally, the consumer is able to visually inspect the article that decreases the consumer's need to open the package in the store. Thus, the window 10 improves the communicational aspects to the consumer of the article 6 inside of the container 27.

As shown in FIG. 1, the window 10 must be clear or substantially clear to see the article's performance characteristic or a portion of the article's performance characteristic. Within the context of this description, the window 10 is "clear" if it provides the consumer the capability of looking though the window 10 to view the article 6 or a portion of the article's performance characteristic. The term "clear" refers to the material capability of transmitting light so that the component, or a portion thereof, can be seen as clearly as if there were no intervening material between the component and the perceiver. Furthermore, the "see-through" clarity indicates the degree of distortion of an object that can be seen through a film. (See The Wiley" Encyclopedia of packaging technology). The material for the window 10 is clear or "substantially clear" when light readily passes through, such that the performance characteristic located opposite the clear material can be viewed by the naked eye. The window 10 can be "substantially clear" when the window is frosted or not frosted in a matte or gloss finish.

Blown, cast, coextrusion, and laminations can be used for extruding a clear film that gives the advantage to print and leaves an area uncovered for a window. A possible window material can be any blend of polymer with no added pigments.

An additional window 11 may also be located on any part of the exterior of the container 27 to act as a repurchase indicator. Specifically, a repurchase indicator provides the consumer a visual means to indicate the amount of product in the package. The window 11 can be located anywhere on the container 27. The window 11 may be the entire container 27 or any portion of the container 27. The window 11 may have a measuring means of the articles 6 on the container 1 which indicates the amount of articles left in the container 27. The measuring means may be any means known in the art. The measuring means may be a line indicator 20. The window 11 allows the consumer to easily determine the amount of article 6 left in the container. As a result, the consumer can determine their need to acquire more of the particular article. For example, as shown in FIG. 1, the line indicator 20 indicates to the consumer that eight sanitary napkins are left in the container 27.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A package comprising:
    a container comprising a layer having an interior surface and an exterior surface, said layer forming an interior space;
    said container comprising a window on only a portion of the exterior surface;
    said container containing in said interior space a plurality of absorbent articles consisting of absorbent articles that are the same type, each having a thickness and substantially the same absorbent capacity, each absorbent article being individually wrapped in a wrapper; and
    said exterior surface of said container comprises a signal color corresponding to the absorbent capacity, and each of said wrappers comprises a substantially similar signal color in the form of a design, wherein at least a portion of said thickness of at least one of said absorbent articles and at least a portion of said signal color can be viewed through said window.

2. The package of claim 1, wherein said design comprises one or more shapes.

3. The package of claim 1, wherein said color is selected from the group consisting of: blue, green, orange, yellow, lavender, violet, purple, and pink.

4. The package of claim 1, wherein said signal color and said substantially similar signal color are the same color.

5. The package of claim 1, wherein said window is provided on a side of the container in the form of a shape.

6. The package of claim 1, wherein said absorbent capacity is light, regular, medium, super, super plus, or overnight.

7. The package of claim 1, wherein the layer comprises a clear film that is printed, wherein the film includes an uncovered area that forms the window.

8. A package comprising:
    a container comprising a layer having an interior surface and an exterior surface, said layer forming an interior space;
    said container comprising a window on only a portion of a side of the container;
    said container containing in said interior space a plurality of catamenial absorbent articles consisting of catamenial absorbent articles that are the same type, each having substantially the same absorbent capacity, each catamenial absorbent article being individually wrapped in a wrapper; and
    said exterior surface of said container comprises a signal color corresponding to the absorbent capacity, and each of said wrappers comprises a substantially similar signal color in the form of a design, wherein at least a portion of said thickness of at least one of said absorbent articles and at least a portion of said signal color can be viewed through said window.

9. The package of claim 8, wherein said design comprises one or more shapes.

10. The package of claim 8, wherein said color is selected from the group consisting of: blue, green, orange, yellow, lavender, violet, purple, and pink.

11. The package of claim 8, wherein said signal color and said substantially similar signal color are the same color.

12. The package of claim 8, wherein said window is provided in the form of a shape.

13. The package of claim 8, wherein said absorbent capacity is light, regular, medium, super, super plus, or overnight.

14. A package comprising:
    a container comprising a layer having an interior surface and an exterior surface, said layer forming an interior space;
    said container comprising a clear window on only a portion of the container;
    said container containing in said interior space a plurality of catamenial absorbent articles consisting of catamenial absorbent articles that are the same type, each having substantially the same absorbent capacity, each catamenial absorbent article being individually wrapped in a wrapper; and
    said exterior surface of said container comprises a signal color corresponding to the absorbent capacity, and each of said wrappers comprises a substantially similar signal color in the form of a design, wherein at least a portion of said thickness of at least one of said absorbent articles and at least a portion of said signal color can be viewed through said window.

15. The package of claim 14, wherein said design comprises one or more shapes.

16. The package of claim 14, wherein said color is selected from the group consisting of: blue, green, orange, yellow, lavender, violet, purple, and pink.

17. The package of claim 14, wherein said signal color and said substantially similar signal color are the same color.

18. The package of claim 14, wherein said window is provided on a side of the container in the form of a shape.

19. The package of claim 14, wherein said absorbent capacity is light, regular, medium, super, super plus, or overnight.

20. The package of claim 14, wherein the layer comprises a clear film that is printed, wherein the film includes an uncovered area that forms the window.

* * * * *

UNITED STATES PATENT AND TRADEMARK OFFICE
CERTIFICATE OF CORRECTION

| | | |
|---|---|---|
| PATENT NO. | : 7,946,420 B2 | Page 1 of 1 |
| APPLICATION NO. | : 12/714952 | |
| DATED | : May 24, 2011 | |
| INVENTOR(S) | : Molina et al. | |

It is certified that error appears in the above-identified patent and that said Letters Patent is hereby corrected as shown below:

<u>Column 1</u>

Line 9, delete "U.S. patent Ser. No." and insert --now Pat. No--.

Line 10, delete "U.S. Pat. No. 7,185,761".

Line 11, insert the word --now-- in front of U.S. Pat.

Line 13, insert the word --now-- in front of U.S. Pat.

Signed and Sealed this
Twenty-seventh Day of March, 2012

David J. Kappos
*Director of the United States Patent and Trademark Office*